United States Patent
Schulze-Ganzlin (10) Patent No.: US 12,257,097 B2
(45) Date of Patent: Mar. 25, 2025

(54) MEASUREMENT AND DATA COMMUNICATION DEVICE FOR AN INTRAORAL DENTAL RADIOLOGY SYSTEM

(71) Applicant: DENTSPLY SIRONA Inc., York, PA (US)

(72) Inventor: Ulrich Schulze-Ganzlin, Lorsch (DE)

(73) Assignee: Dentsply Sirona Inc., York, PA (US)

( * ) Notice: Subject to any disclaimer, the term of this patent is extended or adjusted under 35 U.S.C. 154(b) by 399 days.

(21) Appl. No.: 17/634,090

(22) PCT Filed: Aug. 12, 2020

(86) PCT No.: PCT/EP2020/072666
§ 371 (c)(1),
(2) Date: Feb. 9, 2022

(87) PCT Pub. No.: WO2021/028497
PCT Pub. Date: Feb. 18, 2021

(65) Prior Publication Data
US 2022/0346745 A1 Nov. 3, 2022

(30) Foreign Application Priority Data
Aug. 12, 2019 (EP) .................................... 19000371

(51) Int. Cl.
*A61B 6/00* (2024.01)
*A61B 6/06* (2006.01)
(Continued)

(52) U.S. Cl.
CPC .................. *A61B 6/56* (2013.01); *A61B 6/06* (2013.01); *A61B 6/405* (2013.01); *A61B 6/4266* (2013.01);
(Continued)

(58) Field of Classification Search
CPC ......... A61B 6/06; A61B 6/405; A61B 6/4266; A61B 6/4411; A61B 6/4494; A61B 6/512; A61B 6/542; A61B 6/547; A61B 6/56

See application file for complete search history.

(56) References Cited

U.S. PATENT DOCUMENTS 7,006,600 B1 * 2/2006 Krema ................... A61B 6/465
378/98.7
9,314,216 B2 * 4/2016 De Godzinsky ....... A61B 6/542
(Continued)

FOREIGN PATENT DOCUMENTS

CN 101765291 A 6/2010
CN 107330952 A 11/2017
(Continued)

OTHER PUBLICATIONS

Chinese Office Action dated May 12, 2024.
(Continued)

*Primary Examiner* — Dani Fox
*Assistant Examiner* — Soorena Kefayati
(74) *Attorney, Agent, or Firm* — SCHWEGMAN LUNDBERG & WOESSNER, P.A.

(57) ABSTRACT

A measurement and data communication device for use in or with an intraoral dental radiology system comprising: an x-ray data management unit having a first communication means for retrieving at least x-ray exposure data, and a processing means for processing at least the retrieved data; an intraoral x-ray generation unit having an x-ray source for exposing at least part of a patient jaw with x-rays; and an intraoral x-ray acquisition unit having a first x-ray sensor for acquiring x-ray image data of at least part of the patient jaw. The device further includes: a measurement unit for measuring features related to the x-rays used for exposing at least part of the patient, the measurement unit being
(Continued)

arranged between the x-ray source and the patient; and a second communication means for transmitting the x-ray exposure data which includes the measured features to the x-ray data management unit.

17 Claims, 3 Drawing Sheets

(51) Int. Cl.
*A61B 6/40* (2024.01)
*A61B 6/42* (2024.01)
*A61B 6/51* (2024.01)

(52) U.S. Cl.
CPC .......... *A61B 6/4411* (2013.01); *A61B 6/4494* (2013.01); *A61B 6/512* (2024.01); *A61B 6/542* (2013.01); *A61B 6/547* (2013.01)

(56) References Cited

U.S. PATENT DOCUMENTS

| | | | | |
|---|---|---|---|---|
| 2005/0242269 A1* | 11/2005 | Hayashi | .................... | H04N 5/32 |
| | | | | 348/E5.081 |
| 2006/0188065 A1* | 8/2006 | Razzano | ................ | A61B 6/566 |
| | | | | 378/98 |
| 2006/0188070 A1* | 8/2006 | Razzano | .............. | A61B 6/4233 |
| | | | | 378/168 |
| 2007/0269002 A1* | 11/2007 | Mazuir | .................... | H05G 1/54 |
| | | | | 378/38 |
| 2010/0067650 A1* | 3/2010 | Arai | ........................ | A61B 6/542 |
| | | | | 378/19 |
| 2010/0102241 A1* | 4/2010 | Zeller | .................... | H01L 27/146 |
| | | | | 378/38 |
| 2010/0177865 A1* | 7/2010 | Yoshimura | ............... | A61B 6/51 |
| | | | | 378/19 |
| 2011/0274332 A1* | 11/2011 | Crucs | ...................... | A61B 6/51 |
| | | | | 382/132 |
| 2012/0218544 A1* | 8/2012 | Razzano | .............. | G01B 11/272 |
| | | | | 356/400 |
| 2014/0010350 A1* | 1/2014 | De Godzinsky | ......... | A61B 6/06 |
| | | | | 378/62 |
| 2014/0169533 A1* | 6/2014 | Razzano | .................. | A61B 6/51 |
| | | | | 378/205 |
| 2015/0250436 A1* | 9/2015 | Hyde | ................. | H01L 27/14623 |
| | | | | 378/62 |
| 2016/0262715 A1* | 9/2016 | Charnegie | .............. | A61B 6/465 |
| 2016/0262716 A1* | 9/2016 | Kravis | .................... | A61B 6/463 |
| 2017/0027532 A1* | 2/2017 | Joshi | ...................... | A61B 6/586 |
| 2017/0164914 A1* | 6/2017 | Kravis | .................... | A61B 6/06 |
| 2017/0188987 A1* | 7/2017 | Liu | ........................ | A61B 6/512 |
| 2017/0303877 A1* | 10/2017 | Abkal | .................... | A61B 6/463 |
| 2018/0061054 A1* | 3/2018 | Abraham | ................ | G06T 7/337 |
| 2018/0132813 A1* | 5/2018 | Lim | ........................ | A61B 6/587 |
| 2018/0253535 A1* | 9/2018 | Miller | .................... | A61B 6/512 |
| 2019/0274643 A1* | 9/2019 | Cano | .................... | A61B 6/0407 |
| 2020/0008760 A1* | 1/2020 | Nishimura | ........... | A61B 6/4435 |

FOREIGN PATENT DOCUMENTS

| | | |
|---|---|---|
| DE | 102007033957 A1 | 1/2009 |
| EP | 3777693 | 2/2021 |
| JP | S63115539 A | 5/1988 |
| JP | 2006320717 A | 11/2006 |
| JP | 2014508617 A | 4/2014 |
| JP | 2017225592 A | 12/2017 |
| WO | 2021028497 | 2/2021 |

OTHER PUBLICATIONS

International Search Report; PCT/EP2020/072666; Oct. 16, 2020 (completed); Nov. 5, 2020 (mailed).
International Preliminary Report on Patentability; PCT/EP2020/072666; Oct. 16, 2020 (completed); Nov. 5, 2020 (mailed).
Written Opinion of the International Searching Authority; PCT/EP2020/072666; Oct. 16, 2020 (completed); Nov. 5, 2020 (mailed).
Japanese Office Action dated May 7, 2024.
"European Application Serial No. 19000371.5, Extended European Search Report mailed Feb. 12, 2020", 5 pgs.

* cited by examiner

MEASUREMENT AND DATA COMMUNICATION DEVICE FOR AN INTRAORAL DENTAL RADIOLOGY SYSTEM

CROSS-REFERENCE TO RELATED APPLICATIONS

This is a National Phase application of International Application No. PCT/EP2020/072666 filed on Aug. 12, 2020, which claims the benefit of and priority to European Application Ser. No. 19000371.5, filed on Aug. 12, 2019, which are herein incorporated by reference for all purposes.

TECHNICAL FIELD OF THE INVENTION

The present invention relates to a radiology system. The present invention more particularly relates to an intraoral dental radiology system.

BACKGROUND OF THE INVENTION

In general, an intraoral dental radiology system comprises an intraoral x-ray generation unit, an intraoral x-ray acquisition unit, and an x-ray data management unit. The intraoral x-ray generation unit has an x-ray source for exposing at least part of a patient jaw with x-rays. The intraoral x-ray acquisition unit has an x-ray sensor for acquiring x-ray image data of at least part of the patient jaw. Different x-ray sensor technologies are available. The x-ray sensor might be a digital sensor or an analogue sensor such as a film or a phosphor plate. In general, a digital scanner is used to scan the analogue sensor and digitize the x-ray image. The x-ray sensor is usually held through a sensor holder which can be placed into the mouth of the patient. The sensor holder also has a ring for aligning the tube head of the x-ray generation unit with the x-ray sensor. The tube head includes the x-ray source. In the field of intraoral dental radiology, user-exchangeable collimators are optionally attached to the tube head of the intraoral X-ray generation unit for limiting the x-ray field. These collimators differ in the size of the usable x-ray field and are adapted to the size of the x-ray sensor. This avoids unnecessary exposure of the patient to x-rays that are not received by the x-ray sensor, and thereby reduces the patient dose. In the field of intraoral dental radiology, user-exchangeable additional extension tubes, e.g. from 20 cm (8 inches) to 30 cm (12 inches) are optionally attached to the tube head to extend the length of the tube head. With a larger source-sensor distance, the geometric aspects of the x-ray imaging can be improved, but in return the dose area product is reduced by a factor of the square of the distance.

For entry in the x-ray control book which is optionally used for quality management purposes, default values are used to determine the x-ray exposure data such as the duration of the x-ray exposure, the intensity of the x-ray field, the beam characteristics of the x-ray field, the type of the collimator, the type of the additional extension tube, the sensor-source distance/alignment, and the dose area product.

A problem with the prior art is that the default x-ray exposure data entered by the user may not always correspond the real x-ray exposure data because the intraoral dental radiology systems on the market do not recognize such x-ray exposure data directly.

US2006188065A1 discloses an intraoral dental radiology system according to prior art.

SUMMARY OF THE INVENTION

An objective of the present invention is to overcome the disadvantages of the prior art in an easy and cost-effective way and provide a measurement and data communication device for use in or with an intraoral dental radiology system.

The present invention provides a measurement and data communication device for use in or with an intraoral dental radiology system. The intraoral dental radiology system comprises: an x-ray data management unit having a communication means (hereinafter first communication means) for retrieving at least x-ray exposure data, and a processing means for processing at least the retrieved data; an intraoral x-ray generation unit having an x-ray source for exposing at least part of a patient jaw with x-rays; and an intraoral x-ray acquisition unit having an x-ray sensor (hereinafter first x-ray sensor) for acquiring x-ray image data of at least part of the patient jaw. The measurement and data communication device comprises: a measurement unit for measuring features related to the x-rays used for exposing at least part of the patient jaw, wherein the measurement unit is arranged between the x-ray source and the said at least part of the patient jaw; and a communication means (hereinafter second communication means) for transmitting the x-ray exposure data which includes the measured features to the x-ray data management unit.

A major advantageous effect of the present invention is that the x-ray exposure data can be correctly determined through the measurement, and easily transmitted to the x-ray data management unit through the measurement and communication device. Thereby, the intraoral dental radiology system can be more securely operated. Another major advantageous effect of the present invention is that an existing intraoral dental radiology system can be equipped with the measurement and communication device to benefit from these advantages.

According to an embodiment of the present invention, the intraoral x-ray generation unit preferably has a tube head which includes the x-ray source. And the measurement and communication device is preferably detachably attachable to the tube head. Thereby, an existing intraoral dental radiology system can be easily retrofitted with the measurement and communication device, and thus the x-ray exposure data can be generated and transmitted to the x-ray data management unit to keep a detailed log of the patient treatment and/or to control exposure of the patient.

According to an embodiment of the present invention, the measurement and communication device preferably has an insert tube as the housing which accommodates the measurement unit and the second communication means. And the insert tube can be detachably attached to the tube head without extending the length of the tube head. In this embodiment, the x-ray exposure data transmitted by the second communication means preferably includes information on the presence/absence or also the type of the insert tube.

According to an embodiment of the present invention, the intraoral x-ray generation unit preferably has an additional extension tube which is detachably attachable to the tube head to extend the length of the tube head. The above-mentioned insert tube is preferably usable with this additional extension tube. The additional extension tube is detachably attachable to the tube head in the state when the insert tube has already been attached to the tube head. In this embodiment, the measurement unit preferably has an extension tube identifier for identifying presence/absence or also type of the additional extension tube. In this embodiment, the exposure data which is transmitted by the second communication means preferably includes information on the presence/absence or also type of the additional extension tube i.e., the length of the additional extension tube. The extension tube identifier may have an electromechanical or optomechanical means for identifying a mechanical feature such as indents and/or projections or the like on the additional extension tube.

According to an alternative embodiment of the present invention, the measurement and communication device preferably comprises an extension tube as the housing instead of the insert tube. The extension tube accommodates the measurement unit and the second communication means. And the extension tube can be detachably attached to the tube head to extend the length of the tube head. Thereby, the source-sensor distance can be optionally increased, and the geometric aspects of the x-ray imaging can be further improved. In this alternative embodiment, the x-ray exposure data transmitted by the second communication means includes information on the presence/absence or also the type of the extension tube, i.e., the length of the extension tube.

According to an embodiment of the present invention, the measurement and communication device preferably has one or more user-exchangeable collimators for selectively limiting the x-ray field to the size of the first x-ray sensor. Thereby unnecessary exposure of the patient to x-rays not received by the x-ray sensor can be avoided or reduced as much as possible. The measurement unit preferably has a collimator identifier for identifying presence/absence or also type of the collimator. The type of the collimator is indicative of at least of its size. The diagonal of the collimator aperture is typically approx. 10 mm larger than the diagonal of the active area of the first x-ray sensor. In this embodiment, the exposure data transmitted by the second communication means includes information on the presence/absence or also type of the collimator. Thereby, the release of the x-ray exposure can be optionally inhibited if the collimator is not suitable for the first x-ray sensor. The user may be informed on the false collimator through a warning signal. This warning signal might be generated through a user interface comprising an acoustic means or an optical means such as an LED or the like. To avoid unnecessarily loading of the tube head, the collimators are preferably very light (<200 g). The measurement and communication device is also manufactured as light as possible to allow easy manipulation of the tube head which is arranged on a movable arm.

According to an embodiment of the present invention, the intraoral x-ray acquisition unit preferably has a sensor holder for holding the first x-ray sensor and a ring for positioning the tube head. The ring may also be used to align, the insert tube, the extension tube or the additional extension tube as mentioned above. The measurement and communication device is preferably rotatable around the center of the ring for facilitating the alignment. The ring may have a form fitting member for form-fittingly engaging with a counterpart form-fitting member on one of the tube head, the additional extension tube of the tube head, or the measurement and communication device. The form fitting-member may be round shaped or rectangular shaped. Other shapes may be alternatively used. The measurement unit preferably has a distance measurement means for measuring the distance of the x-ray source to the ring or to the patient. In this embodiment, the x-ray exposure data transmitted by the second communication means includes information on the measured distance. The distance measurement can be performed acoustically or optically with an ultrasound transceiver or infrared transceiver. The release of the x-ray exposure can be optionally inhibited if the distance is not suitable for the targeted region of the patient.

According to an embodiment of the present invention, the measurement unit preferably has a position and alignment measurement means for determining the position of the x-ray source and the alignment of the central beam of the x-ray field relative to a horizontal plane. In this embodiment, the x-ray exposure data transmitted by the second communication means includes information on the determined position and alignment. This allows to register the targeted region of the patient to be exposed to x-rays into a control book as left, middle or right part of the jaw as well as upper or lower part of the jaw. The release of the x-ray exposure can be optionally inhibited if the determined position or alignment is not suitable for the targeted region of the patient. The user may be informed on the misalignment by a warning signal through the user interface. The determination of the position and the alignment can be performed for instance through a Hall angle sensor, a gyroscope or compass sensor.

According to an embodiment of the present invention, the measurement and data communication device preferably has a separate power supplying means which has a motion sensor for activating the supply of power upon sensing motion. For instance, when the insert tube/extension tube is attached to the tube head or moved together with the tube head for alignment, then the power supply may be activated. To save energy, the supply of power may be deactivated upon elapse of a predetermined duration or through the x-ray data management unit via the first communication means when the exposure is terminated. The device may also have a user control panel. The power supplying means may include a mains power cord or one or more batteries, preferably rechargeable batteries. These batteries can be recharged with an external charging unit without having to be removed from the measurement and data communication device. The energy transfer between the external charging unit and the batteries can be realized through flexible cables, electrical pin contacts and/or wireless means such as inductive means. The external charging unit may be portable or installable on a surface, preferably on the wall surface in a practice. The tube head can be relatively moved together with the measurement and communication device to the external charging unit.

According to an embodiment of the present invention, the measurement unit preferably has an x-ray sensor (hereinafter second x-ray sensor) for sensing the duration of the x-ray exposure, intensity of the x-rays, and/or the beam characteristics of the x-rays such as the x-ray tube voltage/current. In this embodiment, the exposure data transmitted by the second communication means preferably includes information on the duration of the x-ray exposure, the intensity of the x-rays, and/or the beam characteristics of the x-rays. The second x-ray sensor is arranged at a position where it does not obstruct x-rays exposing the targeted area of the patient.

The present invention also provides an intraoral dental radiology system which comprises: the intraoral x-ray generation unit having the x-ray source for exposing at least part of a patient jaw with x-rays; and the intraoral x-ray acquisition unit having the first x-ray sensor for acquiring x-ray image data of at least part of the patient jaw, the measurement and data communication device; and the x-ray data management unit which comprises: the first communication means adapted to retrieve the exposure data transmitted by the measurement and data communication device; and the processing means adapted to process the retrieved data.

According to an embodiment of the present invention, the first communication means of the x-ray data management unit preferably retrieves, in addition to the x-ray exposure data, the x-ray image data which is read from the first x-ray sensor. The intraoral x-ray acquisition unit has a communication means (hereinafter the third communication means) for transmitting the x-ray image data to the x-ray data management unit. If the first x-ray sensor is a digital sensor then the x-ray image data is read through a reading means, and transmitted. If the first x-ray sensor is an analogue sensor then the x-ray image is scanned and digitized through a digital scanning means and transmitted.

According to an embodiment of the present invention, the intraoral x-ray generation unit preferably has a communication means (hereinafter the fourth communication means). The processing means of the x-ray management unit is preferably further adapted to control the intraoral x-ray generation unit based on the x-ray exposure data via the fourth communication means. Thereby, the intraoral x-ray generation unit can be more securely operated. For instance, the processing means is preferably further adapted to control the exposure duration, the tube voltage and/or tube current of the x=ray source based on the x-ray exposure data. Thereby, the patient can be more securely handled. For instance, the processing means is preferably further adapted to inhibit release of the x-ray exposure by the intraoral x-ray generation unit if the identified collimator is not suitable for the first x-ray sensor, or the determined position and alignment of the tube head, or the measured distance of the patient is not suitable for the targeted region. In addition, the user may be acoustically and/or optically informed on such abnormalities.

According to an embodiment of the present invention, the x-ray data management unit is preferably adapted to evaluate the dose area product or any other information based on the x-ray exposure data.

According to an embodiment of the present invention, the x-ray data management unit preferably has a data storage means. The x-ray data management unit is preferably further adapted to record the acquired x-ray image data, the x-ray exposure data, patient information and/or other information evaluated based on the x-ray exposure data into the data storage means.

According to an embodiment of the present invention, the first to fourth communication means are preferably adapted for wireless communication. Alternatively, wired communication may be preferably used in any one of the first to fourth communication means. Alternatively, the communication between the first and the second communication means can be performed indirectly via either the third or the fourth communication means.

BRIEF DESCRIPTION OF THE DRAWINGS

In the subsequent description, further aspects and advantageous effects of the present invention will be described in more detail by using exemplary embodiments and referring to the drawings, wherein FIG. 1—are schematic perspectives views of a first embodiment and a second embodiment of the measurement and data communication device each prior to attachment to the tube head of the intraoral dental radiology system.

The reference numbers shown in the drawings denote the elements as listed below and will be referred to in the subsequent description of the exemplary embodiments:
  10. Measurement and data communication device
  11. Measurement unit
  11a. Extension tube identifier
  11b Collimator identifier
  11c. Distance measurement means
  11d. Position and alignment measurement means
  11e. Second x-ray sensor
  12. Second communication means
  13. Insert tube
  14. Extension tube
  15. Collimator
  16. Power supplying means
  20. X-ray data management unit
  21. First communication means
  22. Processing means
  23. Data storage means
  30. Intraoral x-ray generation unit
  31. X-ray source
  32. Tube head
  33. Additional extension tube
  34. Fourth communication means
  40. Intraoral x-ray acquisition unit
  41. First x-ray sensor
  42. Third communication means
  43. Sensor holder
  44. Ring
  100. Intraoral dental radiology system

DETAILED DESCRIPTION OF THE INVENTION

Figure 1:
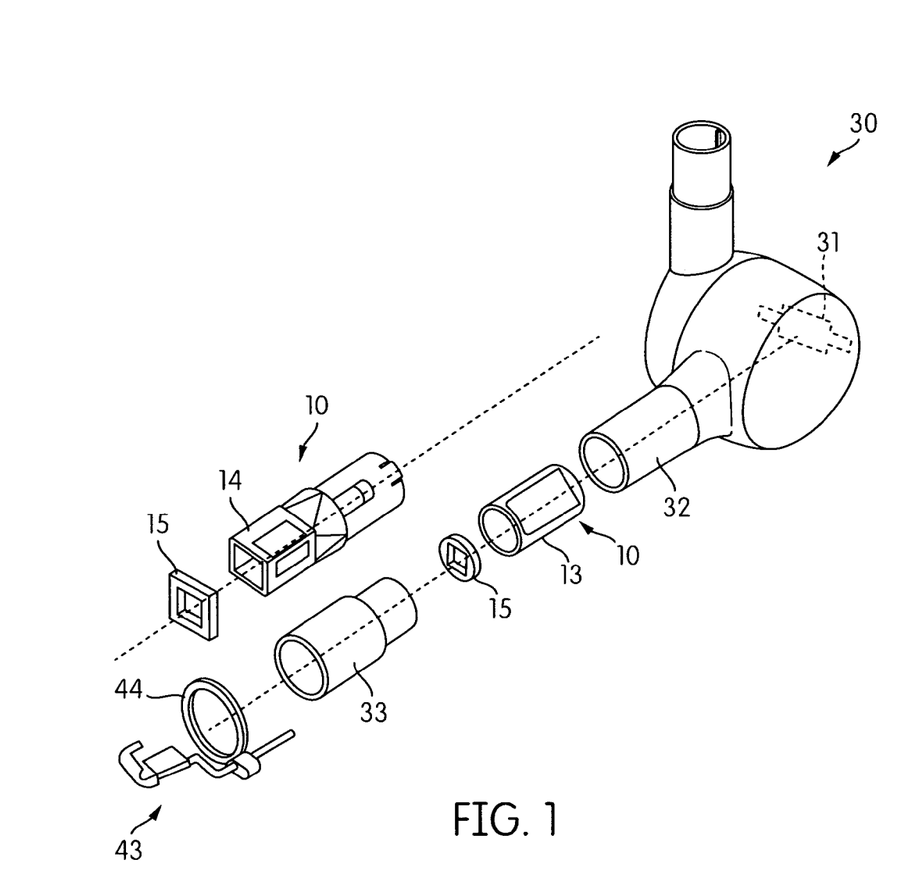
Figure 2:
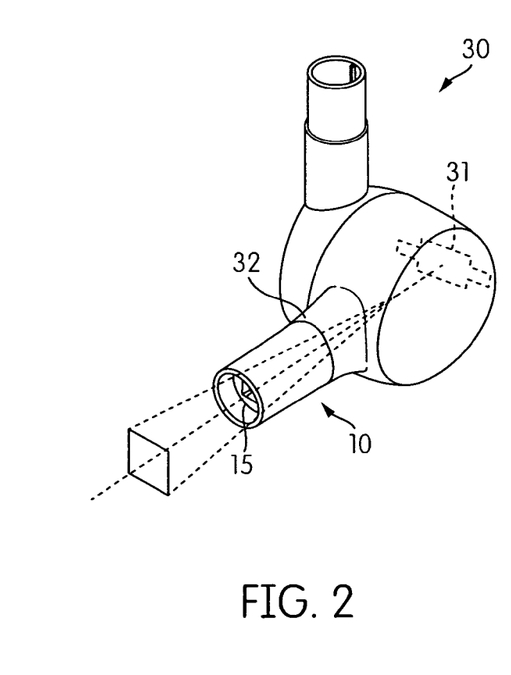
FIG. 2—is a schematic perspective view of the first embodiment of the measurement and data communication device of FIG. 1 after attachment to tube head of the intraoral dental radiology system.
Figure 3:
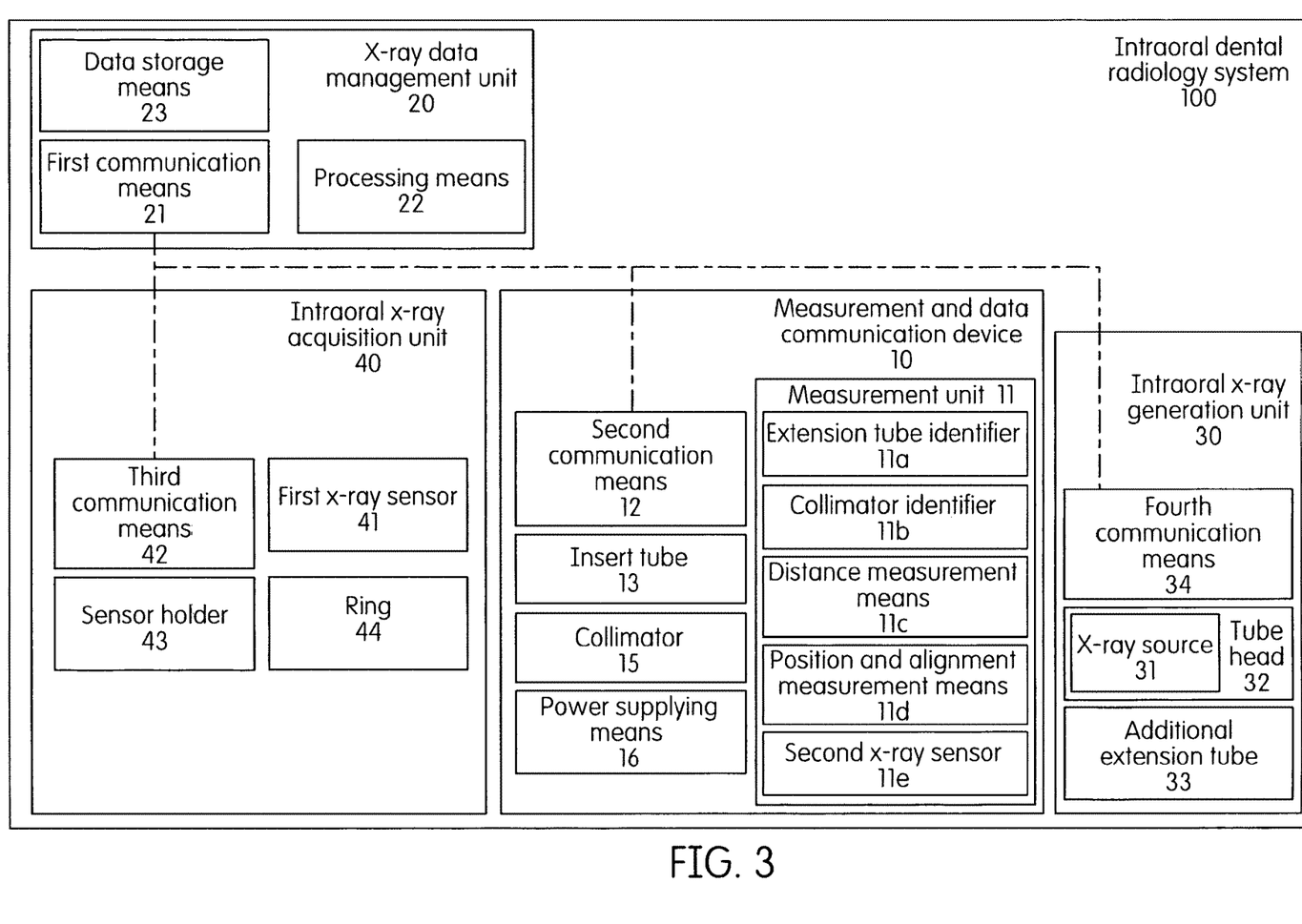
FIG. 3—is a schematic block view of the intraoral dental radiology system retrofitted with the measurement and data communication device according to the first embodiment of the present invention.

FIG. 3 illustrates a block diagram of an intraoral dental radiology system (100) according to a first embodiment. The intraoral dental radiology system (100) has a measurement and data communication device (10), an x-ray data management unit (20), an intraoral x-ray generation unit (30), and an intraoral x-ray acquisition unit (40). The measurement and data communication device (10) has a measurement unit (11) which is arranged between the intraoral x-ray generation unit (30) and the intraoral x-ray acquisition unit (40). The intraoral x-ray generation unit (30) has an x-ray source (31) for exposing at least part of a patient jaw with x-rays. The intraoral x-ray acquisition unit (40) has a first x-ray sensor (41) for acquiring x-ray image data of at least part of the patient jaw. The measurement unit (11) is specifically arranged between the x-ray source (31) and the patient. The measurement unit (11) is adapted to measure features related to the x-rays used for exposing at least part of the patient. The x-ray data management unit (20) and the measurement and data communication device (10) have a first communication means (21) and a second communication means (12) respectively for mutual communication. The first communication means (21) and the second communication means (12) are adapted for wireless communication. The second communication means (12) is adapted to transmit x-ray exposure data which includes the measured features, to the x-ray data management unit (20). The first communication means (21) of the x-ray data management unit (20) is adapted to retrieve at least the x-ray exposure data. The x-ray data management unit (20) has a processing means (22) for processing at least the retrieved data such as the x-ray exposure data. The intraoral dental radiology (100) system is at least partly controlled by the processing means (22). The intraoral x-ray acquisition unit (40) has a third communication means (42) for transmitting the x-ray image data from the first x-ray sensor (41) to the x-ray data management unit (20). The first communication means (21) of the x-ray data management unit (20) is further adapted to retrieve the x-ray image data. The x-ray data management unit (20) has a data storage means (23) that is adapted to record, the retrieved x-ray image data, the x-ray exposure data, patient information and/or other information such as dose area products evaluated through the processing means (22) based on the x-ray exposure data. The intraoral x-ray generation unit (30) has a fourth communication means (34). The processing means (22) is further adapted to control the intraoral x-ray generation unit (30) based on the x-ray exposure data through the fourth communication means (34). The processing means (22) is further adapted to control the x-ray exposure duration, the x-ray tube voltage and/or x-ray tube current of the x-ray source (31) of the intraoral x-ray generation unit (30) based on the exposure data. The processing means (22) is further adapted to inhibit release of the x-ray exposure by the intraoral x-ray generation unit (30) if any abnormality through the x-ray exposure data is identified. Potential abnormalities will be explained later. FIG. 2 is a partial perspective view of the intraoral dental radiology system (100), especially of the intraoral x-ray generation unit (30) according to the first embodiment. The intraoral x-ray generation unit (30) is connectable from its upper part to a movable arm (not shown). The intraoral x-ray generation unit (30) has a tube head (32) which includes the x-ray source (31). The measurement and communication device (10) is detachably attachable to the tube head (32), preferably through complete insertion into the tube head (32). FIG. 2 illustrates the measurement and data communication device (10) after being attached to the tube head (32). FIG. 1 shows partial perspective views of the first embodiment, and also of an alternative second embodiment of the measurement and communication device (10) respectively arranged along the lower and upper dashed lines, which are both shown in the state detached from the tube head (32). As shown in FIG. 1, the measurement and data communication device (10) according to the first embodiment has an insert tube (13) which accommodates the measurement unit (11) and the second communication means (12). As shown in FIG. 1 and FIG. 2, the insert tube (13) can be detachably attached, specifically inserted into the tube head (32) without extending the length of the tube head (32). The x-ray exposure data transmitted to the first communication means (21) includes information on the presence/absence or also the type of the insert tube (13). As shown in FIG. 1, the intraoral x-ray generation unit (30) according to the first embodiment has an additional extension tube (33) which is detachably attachable to the tube head (32) to extend the length of the tube head (32). The additional extension tube (33) is detachably attachable to the tube head (32) in the state when the insert tube (13) has been already attached to the tube head (32). Alternatively, the insert tube (13) can be attached to the additional extension tube (33), specifically through complete insertion into the large diameter portion of the additional extension tube (33) in the state when the additional extension tube (33) has been already attached to the tube head (32) through its low diameter portion. As shown in FIG. 3, the measurement unit (11) has an extension tube identifier (11*a*) for identifying presence/absence or also type of the additional extension tube (33). The x-ray exposure data transmitted to the first communication means (21) includes information on the presence/absence or also type of the additional extension tube (33). As shown in FIG. 1, the measurement and data communication device (10) according to the first embodiment has a user-exchangeable collimator (15) for limiting the x-ray field to the size of the first x-ray sensor (41). As shown in FIG. 3, the measurement unit (11) has a collimator identifier (11*b*) for identifying presence/absence or also type of the collimator (15). The type of the collimator (15) is indicative of at least its size. The processing means (22) is further adapted to inhibit release of x-ray exposure by the intraoral x-ray generation unit (30) if the identified collimator (15) is not suitable for the first x-ray sensor (41). The x-ray exposure data transmitted to the first communication means (21) includes information on the presence/absence or also type of the collimator (15). Thereby, the x-ray exposure data includes the previously mentioned abnormality relating to the collimators (15). As shown in FIG. 1, the intraoral x-ray acquisition unit (40) has a sensor holder (43) for holding the first x-ray sensor (41), and a ring (44) for positioning the tube head (32). As shown in FIG. 3, the measurement unit (11) has a distance measurement means, (11*c*) for measuring the distance of the x-ray source (31) to the ring (44) or to the patient. The exposure data transmitted to the first communication means (21) includes information on the measured distance. The release of the x-ray exposure can be optionally inhibited if the distance is not suitable for the targeted region of the patient. As shown in FIG. 3, the measurement unit (11) comprises a position and alignment measurement means (11*d*) for determining the position of the x-ray source (31) and the alignment of the central beam of the x-ray field relative to a horizontal plane. The alignment comprises the azimuthal angle and the polar angle. The x-ray exposure data transmitted to the first communication means (21) includes information on the determined position and alignment. The processing means (22) is adapted to inhibit release of x-ray exposure by the intraoral x-ray generation unit (30) if the determined position and alignment is not suitable for the targeted region. Thereby, the x-ray exposure data includes the previously mentioned abnormality relating to the position and alignment. As shown in FIG. 3, the measurement and data communication device (10) has a power supplying means (16) which has a motion sensor for activating the supply of power upon sensing any motion. As shown in FIG. 3, the measurement unit (11) has a second x-ray sensor (11*e*) for measuring the duration of the x-ray exposure, intensity of the x-rays, and/or the beam characteristics of the x-rays. The x-ray exposure data transmitted to the first communication means (21) includes information on the duration of the x-ray exposure, the intensity of the x-rays, and/or the beam characteristics of the x-rays. It is also conceivable that the communication between the first communication means (21) and the second communication means (12) for transmitting the x-ray exposure data may also be realized indirectly via the third communication means (42) and/or the fourth communication means (34).

Figure 4:
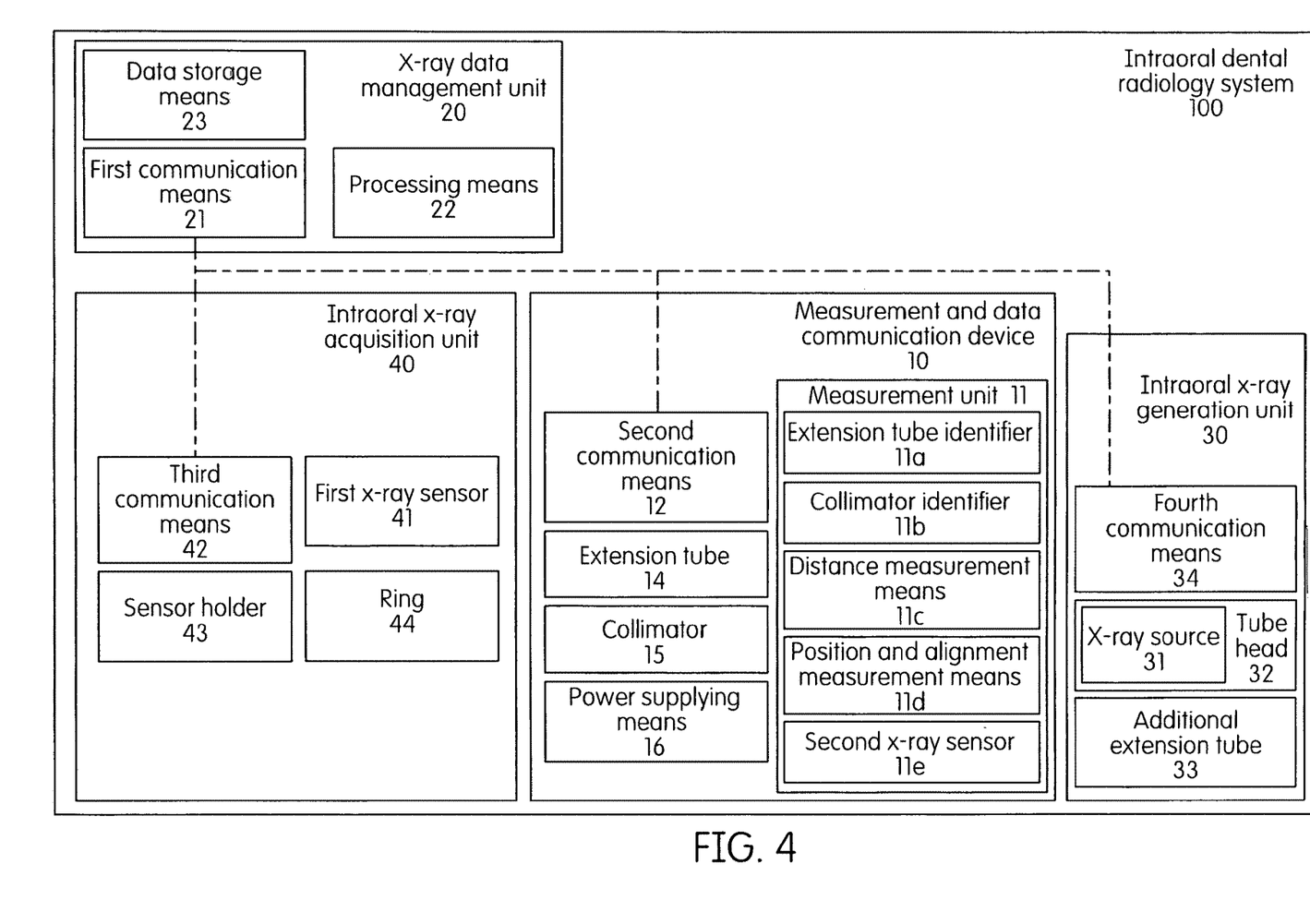
FIG. 4—is a schematic block view of the intraoral dental radiology system retrofitted with the measurement and data communication device according to the second embodiment of the present invention.

FIG. 4 illustrates a block diagram of an intraoral dental radiology system (100) according to the second embodiment. The intraoral dental radiology system (100) of FIG. 4 differs from that of FIG. 3 only in that the measurement and communications device (10) has alternatively an extension tube (14) instead of the insert tube (13). Similar to the first embodiment, the extension tube (14) also accommodates the measurement unit (11) and the second communication means (12). The extension tube (14) can be detachably attached to the tube head (32) to extend the length of the tube head (32). The extension tube (14) may also be detachably attached to the tube head (32) via the additional extension tube (33). The collimators (15) used with the extension tube (14) is preferably rectangular shaped. Alternatively, round shaped collimators (15) may be used. The forward end of the extension tube (14) is rectangular shape. Alternatively, it may have a round shape as the insert tube (13). The x-ray exposure data transmitted to the first communication means (21) includes information on the presence/absence or also the type of the extension tube (14).

The invention claimed is:

1. A measurement and data communication device for use in or with an intraoral dental radiology system including:
    an x-ray data management unit having a first communication device for retrieving at least x-ray exposure data, and a processing means for processing at least the retrieved data;
    an intraoral x-ray generation unit having an x-ray source for exposing at least part of a patient jaw with x-rays; and
    an intraoral x-ray acquisition unit having a first x-ray sensor for acquiring x-ray image data of at least part of the patient jaw;
    said measurement and data communication device comprising:
    a measurement unit configured to measure features related to the x-rays used for exposing at least part of the patient jaw, wherein the measurement unit is arranged between the x-ray source and the patient; and
    a second communication device for transmitting the x-ray exposure data which includes the measured features to the x-ray data management unit;
    wherein the intraoral x-ray generation unit has a tube head which includes the x-ray source, the measurement and data communication device being detachably attachable to the tube head, and
    wherein the measurement and data communication device comprises an insert tube which includes the measurement unit and the second communication device, wherein the insert tube is detachably attachable to the tube head without extending a length of the tube head, wherein the x-ray exposure data further includes information on a presence/absence or a type of the insert tube.

2. The measurement and data communication device according to claim 1 wherein the device has an extension tube which includes the measurement unit and the second communication device, wherein the extension tube is detachably attachable to the tube head to extend a length of the tube head, wherein the x-ray exposure data further includes information on a presence/absence or a type of the extension tube.

3. The measurement and data communication device according to claim 1, wherein the intraoral x-ray generation unit comprises an additional extension tube which is detachably attachable to the tube head to extend the length of the tube head, wherein the additional extension tube is detachably attachable to the tube head in a state when the insert tube or the extension tube is attached to the tube head.

4. An intraoral dental radiology system comprising:
    an intraoral x-ray generation unit having an x-ray source for exposing at least part of a patient jaw with x-rays; and
    an intraoral x-ray acquisition unit having a first x-ray sensor for acquiring x-ray image data of at least part of the patient jaw,
    the intraoral dental radiology system further comprising:
    the measurement and data communication device according to claim 1; and
    the x-ray exposure data being transmitted by the measurement and data communication device.

5. The measurement and data communication device according to claim 3, wherein the measurement unit has an extension tube identifier for identifying the presence/absence or the type of the additional extension tube, wherein the x-ray exposure data further includes information on the presence/absence or the type of the additional extension tube.

6. The measurement and data communication device according to claim 5, further comprising: a user-exchangeable collimator for limiting an x-ray field to a size of the first x-ray sensor; and the measurement unit comprises a collimator identifier for identifying the presence/absence or the type of the collimator, wherein the type of the collimator is indicative of at least a size of the collimator, wherein the x-ray exposure data further includes information on the presence/absence or the type of the collimator.

7. The measurement and data communication device according to claim 6, wherein the intraoral x-ray acquisition unit comprises a sensor holder for holding the first x-ray sensor and a ring for positioning the tube head, wherein the measurement unit comprises a distance measurement means for measuring a distance of the x-ray source to the ring or to the patient, wherein the x-ray exposure data further includes information on the measured distance.

8. The measurement and data communication device according to claim 7, wherein the measurement unit comprises a position and alignment measurement means for determining a position of the x-ray source and the alignment of the central beam of the x-ray field relative to a horizontal plane, wherein the x-ray exposure data further includes information on the determined position and alignment.

9. The measurement and data communication device according to claim 8, further comprising a power supplying means which has a motion sensor for activating the supply of power upon sensing motion.

10. The measurement and data communication device according to claim 9, wherein the measurement unit comprises a second x-ray sensor for measuring one or more of a duration of an x-ray exposure, an intensity of the x-rays, and/or a beam characteristic of the x-rays, wherein the x-ray exposure data further includes information on the duration of the x-ray exposure, the intensity of the x-rays, and/or the beam characteristics of the x-rays.

11. The intraoral dental radiology system according to claim 4, wherein the first communication device and the second communication device are adapted for wireless communication.

12. The intraoral dental radiology system according to claim 11, wherein the first communication device of the x-ray data management unit is further adapted to retrieve the x-ray image data, and the intraoral x-ray acquisition unit has a third communication device for transmitting the x-ray image data to the x-ray data management unit.

13. The intraoral dental radiology system according claim 12, wherein the intraoral x-ray generation unit has a fourth communication device, and the processing means is further adapted to control the intraoral x-ray generation unit based on the x-ray exposure data.

14. The intraoral dental radiology system according to claim 13, wherein the processing means is further adapted to control an x-ray exposure duration, a tube voltage and/or a tube current of the x-ray source of the intraoral x-ray generation unit based on the x-ray exposure data.

15. The intraoral dental radiology system according to claim 14, wherein the processing means is further adapted to inhibit release of x-ray exposure by the intraoral x-ray generation unit responsive to an identified collimator not being suitable for first x-ray sensor, or responsive to the determined position and alignment, or the measured distance not being suitable for a targeted region.

16. The intraoral dental radiology system according to claim 15, wherein the processing means is further adapted to evaluate a dose area product based on the x-ray exposure data.

17. The intraoral dental radiology system according to claim 16, wherein the x-ray data management unit comprises one or more of a data storage device adapted to record the x-ray image data, the x-ray exposure data, patient information and other information evaluated based on the x-ray exposure data.

\* \* \* \* \*